United States Patent
Lampl (10) Patent No.: US 10,765,492 B2
(45) Date of Patent: Sep. 8, 2020

(54) DENTAL VENEERS AND METHODS OF MANUFACTURE

(71) Applicant: Stephan Lampl, Kriessern (CH)

(72) Inventor: Stephan Lampl, Kriessern (CH)

(73) Assignee: Stephan Lampl, Kriessern (CH)

( * ) Notice: Subject to any disclaimer, the term of this patent is extended or adjusted under 35 U.S.C. 154(b) by 205 days.

(21) Appl. No.: 15/855,631

(22) Filed: Dec. 27, 2017

(65) Prior Publication Data

US 2018/0132973 A1 May 17, 2018

Related U.S. Application Data

(60) Division of application No. 13/730,946, filed on Dec. 29, 2012, now abandoned, which is a (Continued)

(30) Foreign Application Priority Data

Jul. 2, 2010 (AT) .................... A 1124/2010

(51) Int. Cl.
*A61C 5/77* (2017.01)
*A61C 5/20* (2017.01)
(Continued)

(52) U.S. Cl.
CPC .................. *A61C 5/77* (2017.02); *A61C 5/20* (2017.02); *A61C 5/70* (2017.02); *A61C 13/087* (2013.01);
(Continued)

(58) Field of Classification Search
CPC ....... C08L 33/10; A61K 6/0023; A61K 6/083; A61K 6/0005; A61K 6/0008;
(Continued)

(56) References Cited

U.S. PATENT DOCUMENTS

| 3,423,823 | A | 1/1969 | Ansley |
| 3,423,828 | A | 1/1969 | Halpern et al. |

(Continued)

FOREIGN PATENT DOCUMENTS

| CN | 1607926 A | 4/2005 |
| DE | 3525720 | 6/1986 |

(Continued)

OTHER PUBLICATIONS

"Selective laser sintering" on Wikipedia, Apr. 1, 2010 (Year: 2010).*
(Continued)

*Primary Examiner* — Matthew J Daniels
*Assistant Examiner* — Yunju Kim
(74) *Attorney, Agent, or Firm* — Workman Nydegger (57) ABSTRACT

A dental veneer made from a composite comprising at least one organic binder, preferably with methacrylate, and inorganic solid particles as fillers. Methods for manufacturing the dental veneer include curing the composite with heat and light under pressure followed by laser treating the facial surface of the veneer to form a smoother facial surface. Filler particles at the facial surface of the veneer can be melted and/or coalesced together to form a continuous glass surface, which is more natural looking and better resembles natural tooth material as compared to ceramic veneers or other composited veneers lacking surface treatment.

18 Claims, 5 Drawing Sheets

Related U.S. Application Data continuation-in-part of application No. PCT/AT2011/000285, filed on Jun. 29, 2011.

(51) Int. Cl.

| | | |
|---|---|---|
| *A61C 5/70* | (2017.01) | |
| *A61C 5/00* | (2017.01) | |
| *A61K 6/16* | (2020.01) | |
| *A61K 6/17* | (2020.01) | |
| *A61K 6/30* | (2020.01) | |
| *A61K 6/77* | (2020.01) | |
| *A61K 6/887* | (2020.01) | |
| *A61C 13/087* | (2006.01) | |

(52) U.S. Cl.
CPC .............. *A61K 6/16* (2020.01); *A61K 6/17* (2020.01); *A61K 6/30* (2020.01); *A61K 6/77* (2020.01); *A61K 6/887* (2020.01)

(58) Field of Classification Search
CPC .. A61K 6/0091; A61K 6/0017; A61C 13/087; A61C 5/00; A61C 5/20; A61C 5/70; A61C 5/77
USPC ......................................................... 264/400
See application file for complete search history.

(56) References Cited

U.S. PATENT DOCUMENTS

| | | | |
|---|---|---|---|
| 3,766,650 A | 10/1973 | Gnecco | |
| 3,986,261 A | 10/1976 | Faunce | |
| 4,226,593 A | 10/1980 | Cohen et al. | |
| 4,433,959 A | 2/1984 | Faunce | |
| 5,080,589 A | 1/1992 | Oden et al. | |
| 5,171,149 A | 12/1992 | Alpert | |
| 5,217,375 A | 6/1993 | Odén et al. | |
| 5,510,066 A | 4/1996 | Fink et al. | |
| RE35,264 E | 6/1996 | Bennett | |
| 5,738,678 A * | 4/1998 | Patel ............... | A61C 1/0046 433/215 |
| 6,382,980 B1 | 5/2002 | Shoher et al. | |
| 6,444,724 B1 | 9/2002 | Stangel et al. | |
| 7,189,076 B1 * | 3/2007 | Rosenfeld .......... | A61C 13/09 433/201.1 |
| 7,691,497 B1 | 4/2010 | Brodkin et al. | |
| 2002/0064749 A1 | 5/2002 | Dietschi et al. | |
| 2003/0125189 A1 | 7/2003 | Castro et al. | |
| 2003/0215770 A1 | 11/2003 | Sekino et al. | |
| 2004/0096805 A1 | 5/2004 | Sueo et al. | |
| 2004/0106087 A1 | 6/2004 | Weigl et al. | |
| 2004/0241609 A1 * | 12/2004 | Jia ................... | A61C 13/0003 433/167 |
| 2005/0069838 A1 | 3/2005 | Kollefrath et al. | |
| 2005/0227204 A1 | 10/2005 | Hauck | |
| 2006/0257823 A1 | 11/2006 | Pfeiffer et al. | |
| 2007/0142495 A1 | 6/2007 | Neffgen et al. | |
| 2007/0231364 A1 | 10/2007 | Nishimoto et al. | |
| 2008/0213727 A1 | 9/2008 | Zhang et al. | |
| 2009/0035723 A1 | 2/2009 | Daniel et al. | |
| 2009/0191512 A1 | 7/2009 | Yarovesky | |
| 2009/0305195 A1 | 12/2009 | Jones et al. | |
| 2010/0021867 A1 | 1/2010 | Altshuler et al. | |
| 2011/0104643 A1 | 5/2011 | Giordano | |
| 2011/0207087 A1 | 8/2011 | Jones et al. | |
| 2012/0276503 A1 | 11/2012 | Wang et al. | |
| 2013/0115573 A1 | 5/2013 | Lampl | |
| 2013/0180110 A1 | 7/2013 | Schechner et al. | |
| 2013/0216787 A1 | 8/2013 | Yeh et al. | |
| 2013/0224688 A1 | 8/2013 | Mayr et al. | |
| 2013/0273501 A1 | 10/2013 | Cascone et al. | |
| 2015/0104665 A1 | 4/2015 | Beeby | |
| 2015/0216636 A1 | 8/2015 | Nakamura et al. | |
| 2015/0320525 A1 | 11/2015 | Lin et al. | |
| 2016/0008093 A1 | 1/2016 | Lampl | |
| 2017/0143868 A1 | 5/2017 | Huang et al. | |

FOREIGN PATENT DOCUMENTS

| | | |
|---|---|---|
| DE | 19654055 | 7/1998 |
| DE | 19859989 | 7/1999 |
| DE | 19807631 | 8/1999 |
| DE | 10234994 | 2/2004 |
| DE | 102005023106 | 11/2006 |
| EP | 0486774 | 5/1992 |
| EP | 0523545 | 1/1993 |
| EP | 0717976 | 6/1993 |
| EP | 1234567 | 8/2002 |
| EP | 2272458 | 1/2011 |
| JP | H08112296 | 5/1996 |
| JP | 08 112296 A | 7/1996 |
| JP | 201183448 | 4/2011 |
| WO | DM/075071 | 12/2010 |
| WO | WO2012064620 | 5/2012 |

OTHER PUBLICATIONS

Atmadja, G., Depth of Polymerization of Visible Light Activated Composite Resins, Thesis, U. of Sydney, Oct. 1986.

Barnes, et al., Clinical Evaluation of Castable Ceramic Veneers, *J. Esthetic Rest. Dent.*, vol. 4, Issue Supp. s1, pp. 21-26, Dec. 1992 (Abstract).

Bergmann, et al., J. Continuing Dental Education 12, Jahrgang, May 2009, 056 "Komposit—Entscheidend ist dir Rezeptur" with English translation.

Beyak, et al., Compatibility of elastomeric impression materials for use as soft tissue casts, *J. Pros. Dent*, vol. 76, Issue 5, pp. 510-514, Nov. 1996 (Abstract).

Catalogue Heraeus Kulzer GmbH, "Pala Mix & Match" 16 pages. Feb. 2011.

Catalogue Bredent visio.lign. German with English translation, 24 pages, Jul. 2009.

Catalogue Bredent visio.lign veneering system, 8 pages Jun. 2011.

Catalogue Bredent visio.lign Toolkit Composite Finishing Set, 4 pages, Jan. 2011.

Dietschi, et al., Prefabricated Composite Veneers: Historical Perspectives, Indications and Clinical Application, *The European Journal of Esthetic Dentistry*, vol. 6, No. 2, Summer 2011.

Haas, B.R., Mastique Veneers: A Cosmetic and Financial Alternative in Post-Periodontal Care, *J. of the New Jersey Dental Assn.*, Fall 1982.

Haller, et al., Adhesives, Ullmann's Encyclopedia of Industrial Chemistry, Nov. 12, 2013.

Helpin, et al. Laboratory Technique for the Laminate Veneer Restoration: 1982. The American Academy of Pedodontics, vol. 4, No. 1.

Instructions for use mastique laminates densply, Google Scholar, http://scholar?q=instruction+for+use_mastique (Nov. 11, 2013).

International Search Report dated Jan. 5, 2012, cited in WO 2012-00006.

Jena, et al., Physical properties and clinical characteristics of ceramic brackets: a comprehensive review, Trends in Biomaterials and Artificial Organs, Society for Biomaterials and Artificial Organs ISSN:0971-1198, vol. 20, Issue 2, Jan. 2007.

Komposit (Zahnmedizin) Author Unknown, Date unknown. Text is based in whole or in part on the Flexikon (http://flexikon.doccheck.com) with English translation.

Leary, B.A., The laminate veneer restoration— affordable esthetics for the elderly, *Special Care in Dentistry*, vol. 1, Issue 5, pp. 231-234, Sep. 1981 (Abstract).

Lim, The Marginal Adaptation of 3 Ceramic Veneer Techniques: an In-Vitro Study, Thesis for Masters of Dental Surgery, University of Sydney Dental Library, 1993.

Mastique Laminate Veneer Photographs, 8 Pages.

Mastique laminate veneers: Results after 4 and 10 years of service, http://informahealthcare.com/doi/abs/10.3109/000163595509005988 (Nov. 11, 2013).

Report Health 3, Tooth veneer has her smiling, Ottawa Citizen, Mar. 17, 1981.

Search Report cited in Austrian application No. A 1124/2010.

(56) References Cited

OTHER PUBLICATIONS

Search Report cited in 201480010839.1 dated Jul. 13, 2017.
Thomson Gale, "Porcelain—Background, Raw Materials, The Manufacturing, Quality Control", Dec. 31, 2006, How Products Are Made, vol. I, pp. 1-5.
Walls, et al., Materials Science, The Bond Strength of Composite Laminate Veneers, *J. Dent. Res.,* Oct. 1985.
Walls, et al., Composite laminate veneers: a clinical study, *J. Oral Rehab.,* vol. 15, Issue 5, pp. 439-454, Sep. 1988 (Abstract).
U.S. Appl. No. 13/730,946, filed Dec. 29, 2012, Office Action dated Mar. 11, 2014.
U.S. Appl. No. 13/730,946, filed Dec. 29, 2012, Final Office Action dated Jan. 16, 2015.
U.S. Appl. No. 13/730,946, filed Dec. 29, 2012, Advisory Action dated Apr. 8, 2015.
U.S. Appl. No. 13/730,946, filed Dec. 29, 2012, Office Action dated Mar. 7, 2016.
U.S. Appl. No. 13/730,946, filed Dec. 29, 2012, Final Office Action dated Oct. 7, 2017.
U.S. Appl. No. 13/730,946, filed Dec. 29, 2012, Office Action dated Apr. 6, 2017.
U.S. Appl. No. 13/730,946, filed Dec. 29, 2012, Final Office Action dated Oct. 4, 2017.

* cited by examiner

DENTAL VENEERS AND METHODS OF MANUFACTURE

CROSS-REFERENCE TO RELATED APPLICATION

This application is a division of U.S. patent application Ser. No. 13/730,946, filed Dec. 29, 2012, which is a continuation-in-part of International Patent Application No. PCT/AT2011/000285, filed Jun. 29, 2011, which claims the benefit of Austria Patent Application No. A 1124/2010, filed Jul. 2, 2010, the disclosures of which are incorporated herein by reference in their entirety.

BACKGROUND

1. Field of Invention

The present invention relates to dental veneers and methods of manufacturing dental veneers.

2. Technology Review

Dental veneers are known in the art and are frequently simply called "veneers". They usually represent cup-shaped solid bodies, which are placed as faces upon perhaps previously ground teeth and/or tooth stumps, in order to provide a discolored tooth with the desired look. Here, they generally replace the natural front of the respective tooth.

Dental veneers are typically custom-made for a particle from a ceramic. First the required geometry of the dental veneer is determined via an impression of the ground tooth and/or tooth stump. Second, based on this information, the customized ceramic dental veneer is produced in the lab. Third, the dentist must then mount this dental veneer onto the tooth and/or tooth stump. In the event the dental veneer was not produced with sufficient diligence, a new dental veneer must be produced, because an adjustment to the conditions in the mouth of the patient by the dentist is not possible on site. This ultimately means that the patient must go to the dentist at least twice, until the fitting dental veneer is produced and mounted to the tooth. Additionally, this leads to the need of lab work with a considerable expense of time and money.

BRIEF SUMMARY

Disclosed herein are dental veneers and methods of making and using such dental veneers. The dental veneers according to the invention relate to solid bodies, which can be placed upon a tooth stump and/or tooth prepared in the manner known from prior art, in order to appropriately cover the front of a discolored tooth and optically improve it. They can be adjusted in size during a single visit to the dentist, can have an appearance that matches the natural look of human teeth, can minimize the amount of natural dental tissue that is removed preparatory to attaching the dental veneer to a person's tooth, and can have a hardness that is similar to the hardness of natural teeth.

The disclosed dental veneers are generally made from composite materials comprising one or more types of binder and one or more types of solid particulate filler. According to one embodiment, the one or more types of binder comprise at least one methacrylate and the one or more types of solid particulate filler comprise solid inorganic particles. Fibers can also be added to the composites to add additional toughness, flexibility and durability. Because the dental veneers are made of composite, they do not have the extreme hardness of ceramic veneers (i.e., about 250 GPa) and are therefore adjustable in size. The hardness of the dental veneers can be similar to that of real teeth (e.g., about 17-20 GPa, preferably about 19 GPa) and be more flexible, less brittle, and more durable and tough than ceramic. This permits the disclosed veneers to be significantly thinner in cross section compared to ceramic veneers. This, in turn, permits less tooth material to be removed during preparation for receiving the veneer.

With regards to their exact size and/or shape, dental veneers as disclosed herein can be adjusted in size and/or shape on site by a dentist using common dental tool and thus be adjusted to the specific tooth conditions of the patient at the time the dental veneer is applied to the tooth surface. This permits production of non-customized dental veneers that can essentially be customized to a patient while at the dental office. This eliminates the need to have customized dental veneers produced in a lab.

According to one embodiment, the exterior surface of the dental veneer is at least partially laser-treated to form a continuously hardened and/or glazed molten layer. The composite from which the dental veneer is made may therefore comprise in specific regions, preferably the exposed outer surface of the dental veneer, a layer which essentially comprises only the continuously hardened or molten material of the solid particles. This yields a dental veneer having a smoother, more glossy exterior finish that is better able to match the look of natural tooth enamel compared to ordinary composite materials used to fill or repair teeth. In addition, and primarily due to the solid particles used as fillers, the disclosed dental veneers can have the required strength and hardness so that said tooth provided with the dental veneer can permanently perform its actual objective as a chewing tool. Moreover, the continuously hardened and/or glazed outer layer provides greater hardness and durability than conventional composites and can better match the hardness and durability of natural tooth enamel.

The composite veneers can also be made according to a novel molding process, described in more detail below. According to one embodiment, the mold used to make the composite veneers can have both transparent (e.g., glass) and non-transparent (e.g., metal) surfaces. The mold can be heated to promote heat curing of the composite resin within the mold. In addition, the transparent surface permits light curing of the composite adjacent to the transparent surface. Such light curing can more quickly cure the composite adjacent to the transparent surface, which advantageously causes more polymerization shrinkage of the composite adjacent to the transparent surface adjacent to the transparent surface. This, in turn, draws the solid filler particles closer together and increases their density prior to laser treatment. The high pressure within the molds can further condense and consolidate the composite material together to increase composite density, strength, durability, glossiness, and other desired properties.

The disclosed dental veneers can be less hard and brittle and have increased toughness compared to conventional ceramic veneers. This permits the dental veneers to advantageously have a thinner profile so that less of the patient's natural tooth tissue needs to be removed preparatory to attaching the veneer. In addition, because they are not as hard as ceramic veneers, the disclosed dental veneers can be more easily adjusted to fit a patient's tooth or teeth, such as by means of a cutting or grinding tool. In addition, because natural tooth surfaces are not always perfectly dimensioned, the disclosed dental veneers can be altered, either before or after placement over a patient's teeth, to have a slightly irregular surface, such as by means of a grinding tool. In this way, they can have a more natural appearance compared to ceramic veneers, which can have an artificial appearance as a result of having a perfectly regular surface.

These and other advantages and features of the invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. The following drawings depict only typical embodiments of the invention and are not therefore to be considered limiting of its scope.

DETAILED DESCRIPTION OF EXEMPLARY EMBODIMENTS

Disclosed herein are dental veneers made from composite materials comprising one or more types of organic binder and one or more types of solid particulate filler. An exterior surface of the dental veneer can be at least partially laser-treated to form a continuously hardened and/or glazed layer on the facial veneer surface. The composite from which the dental veneer is made may comprise at specific sections, preferably the surface of the dental veneer, a layer which consists essentially of only the glazed layer of the solid particles.

With regards to their shape, dental veneers of this type can be processed on site by the dentist using the common tools of his/her practice and thus be adjusted to the conditions given in the patient. This eliminates the necessity of producing the dental veneers in a lab.

Similar to prior veneers, the dental veneers according to the invention have solid bodies, which may be placed upon a tooth stump and/or tooth prepared in manners known in the prior art, in order to appropriately cover the front of a discolored and/or damaged tooth and optically improve it. In one or more embodiments of the invention, dental veneers have solid bodies which are at least partially shaped in a curved cup-like fashion. Primarily due to the solid particles used as fillers, the dental veneers according to the invention also have a required solidity and/or hardness so that said tooth provided with the dental veneer can permanently perform its actual objective as a chewing tool.

In order to achieve high solidity of the dental veneer it is beneficial to arrange the solid particles of the filler packed as densely as possible in the dental veneer. For this purpose it is beneficial for the filler to comprise solid particles with grain sizes different from each other. In one or more embodiments of the invention, the dental veneers comprise macro particles in a range of 50 μm to 1 mm (e.g., about 500 μm), micro particles in a range of 1 μm to 50 μm (e.g., 5 μm), and nano particles in a range of 100 nm to 1 μm (e.g., 500 nm).

In order to achieve a high packing density, particularly small grain sizes are important here, because they fill the spaces between the larger grains. In this sense it is beneficial for the filler to comprise solid particles with grain sizes ranging from about 0.01 μm to about 3 μm. Additionally, in order to achieve higher solidity, the fill level of the composite must be as high as possible, which means the proportion of filler solid particles should be as high as possible (i.e., have high particle packing density). Beneficial variants of the invention provide that the filler solid particles be at least 75% by volume, preferably at least 82% by volume, in the composite of the dental veneer.

In one or more embodiments of the invention, the filler solid particles include glass, a mixture of several types of glass, or materials made therefrom. The types of glass may be different in color and composition. In one or more embodiments, the solid particles may comprise barium glass or strontium glass or mixtures thereof. In other embodiments, the solid particles may comprise aluminium-fluorosilicate glass, strontium-aluminium-silicate glass, barium-aluminium-silicate glass. In general, it may relate to a surface-treated $SiO_2$. In alternative embodiments of the current invention, the solid particles comprise quartz, ceramic, pyrogenic silica, precipitated silica, x-ray opaque dental glasses, ytterbium trifluoride, highly dispersed silica such as $ZrO_2$, $Ta_2O_3$ and $TiO_2$ or mixed oxides of $SiO_2$, $ZrO_2$ and/or $TiO_2$.

The veneers according to the current invention comprise an organic binder. One or more embodiments of the invention use a binder comprising mono-, di- or poly-acrylates and methacrylates. For instance, the organic binder in the composite may be made from one or more of the following: methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, trishydroxyethyl-isocyanurate trimethacrylate, 4,4'-(4,4'-isopropylidene diphenoxy)-bis(hydroxyethyl methacrylate phthalate) (BPDP), bis glycerol dimethacrylate phosphate, bis 2-hydroxy ethyl methacrylate phosphate, p-hydroxyphenyl methacrylamide, 3-hydroxy propyl methacrylate, 4-hydroxy butyl methacrylate, triethylene glycol dimethacrylate (TEG-DMA), alkylhydroxy methacrylates, alkylamino methacrylates, urethane dimethacrylate (UDMA), butane diol dimethacrylate, and bisphenol-A-diglycidyl dimethacrylate (Bis-GMA), diurethane dimethacrylate (DUDMA), hydroxyethyl methacrylate (HEMA), methacrylic acid, and/or glycerol di-methacrylate (GDMA), mono-2-(methacryloyloxy)ethyl succinate (HEMA Succinate), hydroxypropylmethacrylate (HPMA), the bis-acrylates and bis-methacrylates of polyethylene glycols of molecular weight 200-500, copolymerizable mixtures of acrylated monomers, and copolymerizable acrylated oligomers, and the like.

In one or more embodiments of the invention, the organic binder may contain phosphoric acid derivatives and carboxylic acid derivatives of ethylenically unsaturated monomers. In alternative embodiments, the organic binder may comprise vinyl compounds such as styrene, diallyl phthalate, divinyl succinate, divinyl adipate and divinylphthalate.

The disclosed dental veneers are generally made from composite materials comprising one or more types of binder and one or more types of solid particulate filler. According to one embodiment, the one or more types of binder comprise at least one methacrylate and the one or more types of solid particulate filler comprise solid inorganic particles. Fibers can also be added to the composites to add additional toughness, flexibility and durability. Because the dental veneers are made of composite, they do not have the extreme hardness of ceramic veneers (i.e., about 250 GPa) and are therefore adjustable in size. The hardness of the dental veneers can be similar to that of real teeth (e.g., about 17-20 GPa, preferably about 19 GPa) and be more flexible, less brittle, and more durable and tough than ceramic. This permits the disclosed veneers to be significantly thinner in cross section compared to ceramic veneers. This, in turn, permits less tooth material to be removed during preparation for receiving the veneer.

An important objective when mounting dental veneers to teeth and/or tooth stumps is to control the coloring of the veneered tooth such that the conditions in the mouth of the patient are matched, i.e. the color of the veneered tooth is adjusted to the same color as adjacent teeth. In one or more embodiments of the invention, the dental veneer comprises a standard color, which resembles the color of natural tooth enamel. In other embodiments of the invention, the dental veneer is translucent and/or transparent, instead of opaque. In these embodiments, color can be adjusted by using an appropriately colorized bonding material (or bonding material), which is arranged between the dental veneer and the tooth and/or tooth stump when the dental veneer is mounted and shines through the translucent dental veneer. This way the color of the veneer can be adjusted to match the color of the overall environment. Examinations have shown that dental veneer with the following quality are preferable: translucency from about 28% to about 39% and/or a L-value of about 59 to about 69 and/or an a-value from about −0.35 to about −3.2 and/or a b-value from about −0.4 to about −6.95. Translucency relates to the light permeability, i.e. the reciprocal features of opacity. The values mentioned above relate to a measurement according to DIN 6174. The lab-color spectrum is known in prior art. It is designed based on the complementary color theory and allows one to determine a color value using color parameters and color intervals in an approximated uniform CIELAB-color range. The L-value, the a-value, and the b-value are also determined according to DIN 6174. When applying the complementary color theory, a-axis relates to the complementary colors green and red. The b-axis relates to the complementary colors blue and yellow. The L-axis is positioned perpendicularly in reference to this level and reflects brightness.

Based on its high solidity, the dental veneers implemented according to the invention may be made relatively thin. In one or more preferred embodiments of the invention, a dental veneer comprises a cutting edge at one of its end sections, preferably showing a thickness ranging from about 1.0 mm to about 1.3 mm. At regions outside of the cutting edge section, the dental veneer preferably has a thickness of about 0.6 mm, and/or tapers flat at its end opposite the cutting edge. Here, thickness is to be understood as the wall thickness in the respective area of the dental veneer.

One or more embodiments of the invention allow a dentist to adjust a dental veneer and/or a blank of dental veneer on site to match the geometric requirements of the tooth and/or the tooth stump of the patient. In one or more embodiments of the invention, the dentist has the chance to select a bonding material according to its color, thereby he/she can perform the desired color matching on site. A particular embodiment of the invention provides a set (or kit) of several dental veneers with various sizes and/or differently shapes. The set (or kit) additionally comprises at least one liquid or pasty bonding material and several different dyes for coloring the bonding material. In an alternative embodiment, the set (or kit) includes several differently colored, liquid or pasty bonding materials. The provided bonding materials are suitable to fasten or adhere the dental veneer to a tooth and/or a tooth stump.

Having a set of dental veneers as noted above allows the dentist to select a blank of dental veneer that most closely resembles the natural situation of the tooth or tooth stump to be treated. The remaining adjustment can then be performed by processing and/or cutting this blank on site. For this purpose, the dentist can use the cutting tools usually available. Further, the dentist can select the suitable dye and/or the appropriately colored fastening (or bonding) material, by which the dental veneer is fastened or adhered to the tooth stump and/or tooth, so that the desired coloring is achieved in the dental veneer fastened to the tooth and/or tooth stump. In one or more embodiments, the set (or kit) may comprise at least one bonding material and several different dyes by which the bonding material is colored by the dentist. In other embodiments, the set already comprises several differently colored bonding materials, in which the dye no longer needs to be mixed into the bonding material by the dentist. The bonding material may be pasty, i.e. mushy and/or thickly viscous. Organic pigments and/or the inorganic whitener $TiO_2$ may be used as colorants to dye the bonding material.

In order to allow processing smaller fissures it is also possible to provide a liquid bonding material in the set. Particularly preferred embodiments of the set according to the invention provide that the bonding material, preferably provided in a pasty form, comprises the same or similar composite as the dental veneer of the set, however still in the pasty consistency. Further, it is beneficial when the bonding means, particularly provided in a liquid form, comprises the same organic binder as the dental veneer of the set, however still in a liquid form.

Advantageous embodiments of the set according to the invention additionally provide that the set comprises at least one adhesive agent, preferably at least two different adhesive agents, and/or at least one etchant. An adhesive agent serves to create a bond between the hydrophilic tooth and the hydrophobic composite of the dental veneer and/or the bonding means. In a prefer embodiment, the adhesive agent may also compensate shrinking forces of the bonding material. When at least two different adhesive agents are provided, one of them may be used as an adhesive agent between the tooth and the bonding means, and the other adhesive agent may be used between the bonding means and the dental veneer. Non-limiting examples of suitable adhesive agents include the products of the company Indigodental GmbH & Co. KG in Pinneberg, Germany, marked REF 2050 and REF 2051. The product REF 2050 may be used as an adhesive agent between the tooth stump and the bonding material. It includes methacrylated polyacrylic acid in a Bis-GMA based matrix. The product REF 2051 may be used as an adhesive agent between the bonding material and the dental veneer. This also relates to a Bis-GMA based methacrylate.

In one or more embodiments, the etchant is in the form of a corrosive gel, which serves to etch away the residual lubricants caused by the drill of the dentist and to expose the tubuli. Examples of suitable etchants include, but are not limited to, 15-37% concentrated phosphoric acid or the product REF 2052 of the above-mentioned company. It is also possible to use prepared mixtures of etchants and adhesive agents. Generally, the adhesive agents may include low-molecular methacrylates. Additionally, polymers showing a hydrophilic and a hydrophobic end may be used, such as methacrylated polyacrylic acid.

For example, the product of the company Indigodental GmbH & Co. KG in Pinneberg, Germany, available under the name REF 2061, may be used as the composite for the production of dental veneers as well as the bonding means. This product includes tri-ethylene glycol-dimethacrylate, urethane dimethacrylate, Bis-GMA, and ethoxylated biphenol A dimethacrylate. The product REF 2050 of said company, already mentioned with regards to adhesive agents, may be used as the organic binder.

Figure 1:
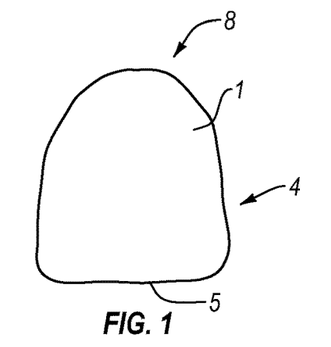
FIGS. 1-3 are frontal views illustrating exemplary dental veneers for teeth of the upper jaw.
Figure 2:
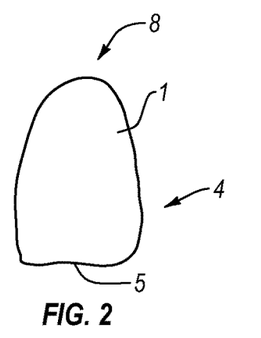
Figure 3:
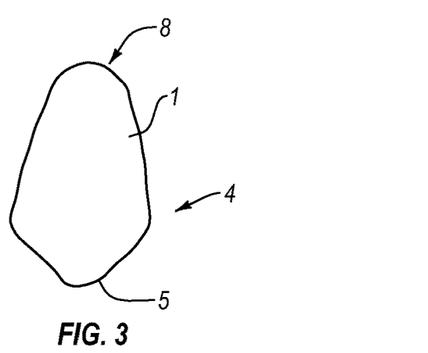
Figure 4:
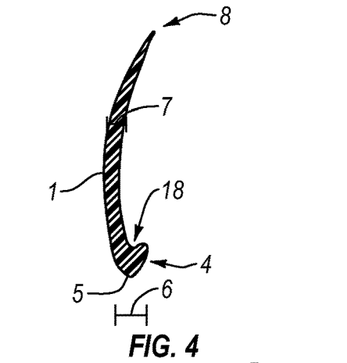
FIGS. 4-6 are longitudinal cross-sectional views through the exemplary dental veneers depicted in FIGS. 1-3, respectively.
Figure 5:
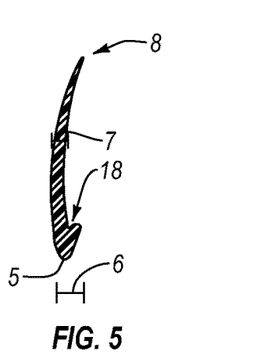
Figure 6:
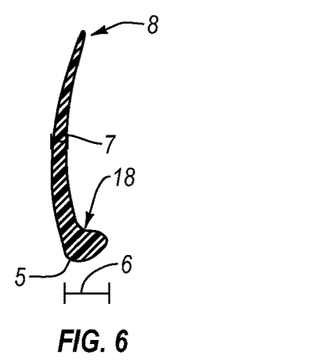
Figure 7:
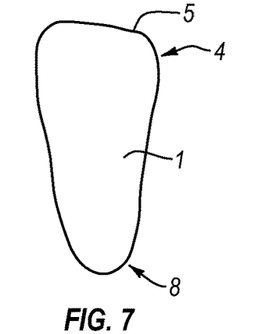
FIGS. 7-9 are frontal views illustrating exemplary dental veneers for teeth of the lower jaw.
Figure 8:
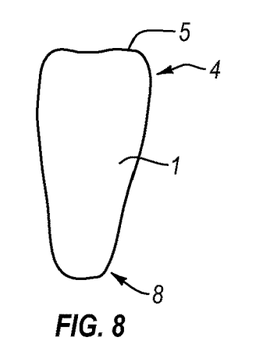
Figure 9:
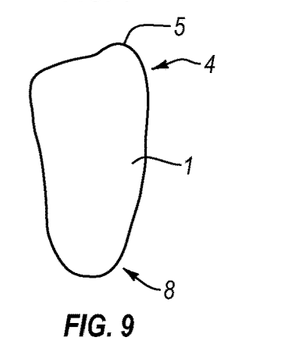
Figure 10:
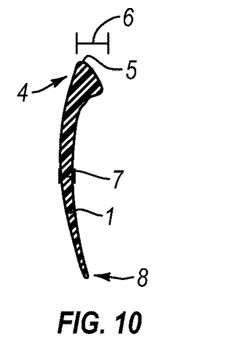
FIGS. 10-12 are longitudinal cross-sectional views through the exemplary dental veneers depicted in FIGS. 4-6, respectively.
Figure 11:
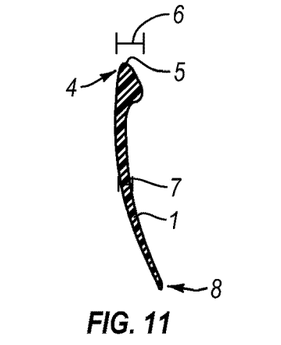
Figure 12:
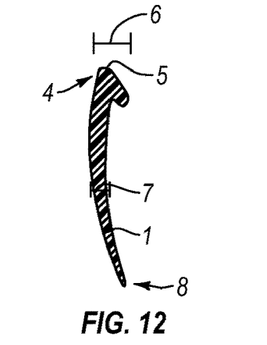

Reference is now made to the drawings. FIGS. 1-3 show various dental veneers 1 for different teeth of the upper jaw. FIGS. 7-9 show various teeth veneers 1 for different teeth of the lower jaw. Experiments have shown that it is possible to generalize the tooth shapes occurring in the majority of different patients such that a relatively small number of differently-shaped blanks of dental veneers 1 can cover almost all naturally occurring forms of teeth if the dentist on site selects the appropriate blank of the dental veneer 1 and adjusts it to the actually given tooth shape of the patient. This kind of onsite customization can be achieved using the dental veneer 1 according to the invention, but is difficult or impossible in the prior art.

Accordingly, a relatively small number of sets of blanks is sufficient in practice. In one embodiment, they may be offered in three different size levels for the upper jaw and two different size levels for the lower jaw. FIGS. 4-6 and 10-12 each show a longitudinal cross-section through the dental veneer 1 of the figure shown thereabove. Each of the dental veneers 1 shown comprises an end section 4 in the area of the cutting edge 5. Here, when chewing, the cutting edge 5 directly contacts the food to be chewed in order to break it apart. As particularly discernible in the longitudinal cross-sections according to FIGS. 4-6 and 10-12, the dental veneer 1 has its greatest thickness 6 in the end section 4 of the cutting edge 5. The thickness preferably ranges from about 1 mm to about 1.3 mm.

In the end section 4, the dental veneers 1 shown in a longitudinal cross-section are embodied as hook-shaped or graduated, at least at the back. In this configuration, the cutting edge 5, when the dental veneer 1 is applied to the tooth stump 10, forms the entire cutting edge of the tooth reconstructed in this manner. As is discernible in FIG. 14, the tooth stump 10 then contacts in a form-fitting manner the free end 18 of the end section 4, embodied hook-shaped and/or graduated as seen in the longitudinal cross-section. Outside the end section 4, the dental veneer 1 shows a considerably thinner thickness 7 as seen in FIGS. 4-6 and 10-12. Preferably, it is no thicker than about 0.6 mm. In the embodiments shown in FIGS. 4-6 and 10-12, the end 8 of a veneer located opposite the cutting edge 5 tapers flat. In one of more embodiments of the invention as seen in FIGS. 1-3 and 7-9, the dental veneer 1 forms an overall shape that is at least partially cup-shaped.

Figure 13:
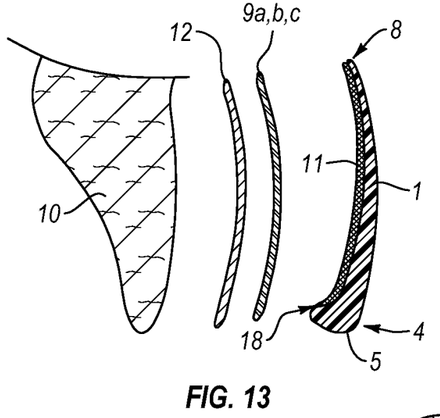
FIG. 13 is a schematic exploded side view illustrating an exemplary application of a dental veneer to a tooth stump.

FIG. 13 shows, in a largely schematic fashion, a dental veneer 10 already prepared and etched. Initially, a first adhesive agent 12 is applied, which provides an intimate connection between the tooth stump 10 and the bonding material 9a, b, or c. Preferably the bonding material is a pasty material. In one or more embodiments, the bonding material comprises the same composite, i.e. an organic binder 2 and solid particles 3, as the one constituting the dental veneer 1. However the bonding material is in a pasty consistency. Additionally, the bonding material can be dyed in order to show through the translucent veneer and provide the desired color when finished and fastened to the tooth.

For a large-area bonding, the bonding material 9b and 9c preferably comprise both the organic binder 2 as well as the solid particles 3. However, this material is relatively mushy and/or pasty as compared to more highly filled composites used to make the veneers. In order to allow the processing of very delicate surface structures, instead of this bonding material 9b and 9c, another bonding material 9a may also be used, which comprises, in addition to the dye, exclusively the organic binder 2 or at least a lower portion of solid particles 3. For instance, the bonding material 9a in one embodiment has 60 to 70% binder by volume. This bonding material 9a may comprise the same organic binder, preferably on a methacrylate basis. The bonding material 9a also has the same type and mixture of solid particles but at a lower concentration than the composite of the finished dental veneer 1.

In one or more preferred embodiment, an adhesive agent 11 is applied between the bonding material 9a, b, or c and the dental veneer 1. It is particularly preferred when this represents an adhesive agent 11 different from the adhesive agent 12. Suitable examples for adhesive agents have been described above.

Figure 14:
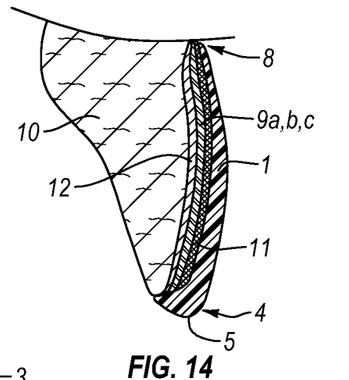
FIG. 14 is a schematic side view of the dental veneer of FIG. 13 applied to the tooth stump.

FIG. 14 shows the finished status, in which the dental veneer 1 is fastened via the bonding material 9a, b, or c to the tooth stump 10, with the adhesive agents 11 and 12 being interposed. The color pigments provided in the bonding material 9a, b, or c can be seen through the translucent material of the dental veneer 1 and thereby provide the desired shade.

Figure 15:
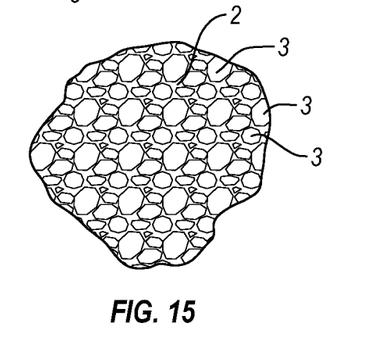
FIG. 15 is a schematic photomicrograph of a composite used in making a dental veneer.

FIG. 15 is a schematic enlargement of the composite material of the dental veneer 1. The various solid particles 3 are intimately connected to each other via the organic binder 2. Preferably methacrylate-based resins are used as organic binders. Examples of a suitable organic binder 2 have been mentioned above. The solid particles 3 preferably comprise a glass mixture with solid particles 3 of different grain sizes. In this manner, the composite material may achieve a higher density (e.g., mass density and/or particle packing density), which leads to higher strength, stability, and resistance to abrasion. Preferably, the solid particles 3 in the dental veneer 1 amounts to at least 75% by volume, and more preferably at least 82% by volume. In order to allow filling the gaps between the relatively large grains as best as possible, preferred embodiments of the invention provide that the grain sizes of at least a portion of the solid particles 3 range from about 0.01 and about 1 mm, preferably from about 0.1 μm to about 500 μm.

Figure 16:
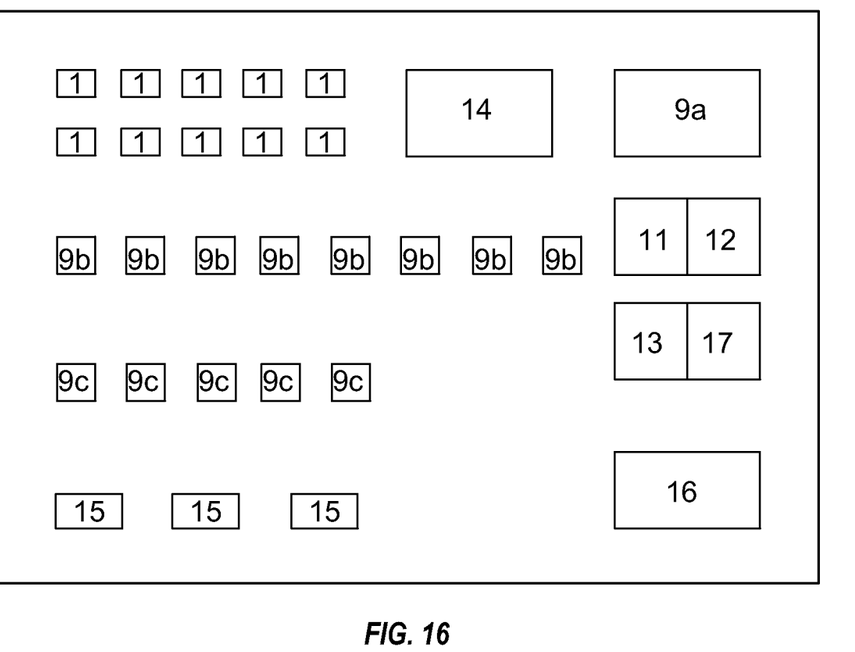
FIG. 16 illustrates an embodiment of an exemplary kit of dental veneers according to the invention.

One aspect of the invention relates to a dental set that allow a dentist to adjust and mount the dental veneer 1 to the tooth stump 10 during a single treatment session. FIG. 16 shows schematically a dental set with several differently sized dental veneers 1 and adjuvants. The dental set according to FIG. 16 comprises various sets of differently sized and shaped dental veneers 1. In one exemplary embodiment, there is one set of dental veneers 1 for the teeth of the upper jaw in three different sizes. For the lower jaw, the dental set may include veneer sets of different shapes, each shape having two different sizes. The difference in size between two closest sizes is preferably about 10%. From this supply of dental veneers 1, the dentist can select the best matching veneer for the respective tooth of the patient and then perform detailed adjustment by an appropriate cutting on site. In order to facilitate the selection of the correct dental veneer 1 by the dentist, the set according to FIG. 16 comprises various forms 15 for matching tooth size, by which the optimally pre-shaped dental veneer 1 can be selected in a simple fashion.

In addition to the dental veneers 1, the dental set according to FIG. 16 also comprises different bonding materials 9a, b, and c. The bonding material 9a is used when the purpose is to fill very small hollow spaces with bonding material. The bonding material 9a comprises an organic binder 2, which may be contained in and dispensed by different syringes and can be variously dyed. In one embodiment, the bonding material 9a may comprise a minor proportion of solid particles 3, preferably in the above-mentioned concentration (i.e., about 60-70% binder and about 30-40% filler). In addition to the color pigments and perhaps additional adjuvants, the bonding material 9a may essentially be equivalent to the organic binder 2, from which the composite of the dental veneer 1 of this set is made. Optionally, it may include an additional small portion of solid particles 3.

The bonding materials 9b and 9c represent differently dyed pasty bonding materials. Preferably, they comprise the composite of the dental veneer 1 in a not yet cured consistency. The bonding materials 9b and 9c therefore comprise both the organic binder 2 as well as the solid particles 3.

With the help of a color key 14 the dentist can select the appropriately dyed bonding material 9a, b, or c and use it in the manner indicated in FIGS. 13 and 14 to fasten or bond the dental veneer 1 to the tooth stump 10. The bonding materials 9c are provided for such cases in which natural tooth enamel remains at the tooth stump 10. The dyes selected here may therefore be very light. The various bonding materials 9b are provided in case the tooth enamel has completely been removed from the tooth stump 10 and more intense dyes can be used to achieve the desired result.

In the exemplary embodiment shown, the dental set (or kit) according to FIG. 16 may also comprise application syringes 16, which serve to apply the bonding material 9a, b, and/or c upon the tooth stump 10. Elements 11 and 12 are two different adhesive agents, which can be used as shown schematically in FIG. 13.

Additionally, the set according to FIG. 16 comprises an etchant 13, which can be used to etch away any layer of lubricants caused by the prior processing of the tooth stump 10 before the respective adhesive agent 11 and/or 12 is applied and to expose the tubuli and/or tooth stumps and/or teeth. In the exemplary embodiment shown, an etch/adhesion means 17 is provided, which represents a combination of etchant and adhesive agent. Preferred embodiments of appropriate sets are offered in the respective containers. Of course, the allocation of the compartments and the content are only shown as examples and schematically in FIG. 16.

Figure 17:
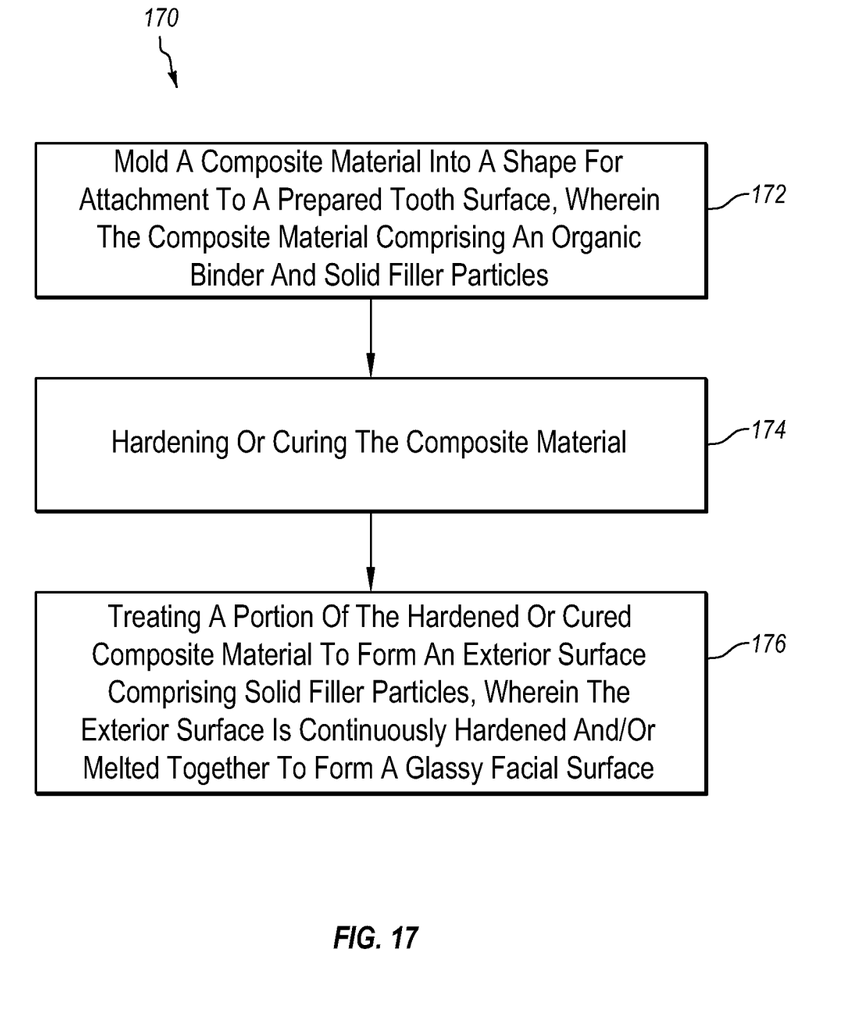
FIG. 17 is a flow diagram that schematically illustrates an exemplary method for molding a dental veneer from a composite material.

Another aspect of the invention relates to methods for manufacturing the dental veneers 1 from the composite material mentioned above. FIG. 17 is a flow diagram that schematically illustrates an embodiment if a general process 170 for manufacturing veneers according to the invention. The first step 172 includes molding a composite material into a shape for attachment to a prepared tooth surface. The composite material may be disclosed above and comprises at least an organic binder and solid filler particles. The next step 174 includes at least partially hardening or curing the composite material. A third step 176 includes treating a portion of the at least partially hardened or cured composite material to form an exterior surface. The exterior surface from this treatment comprises solid filler particles that have been continuously hardened and/or melted together to form a hardened glassy surface.

Figure 18:
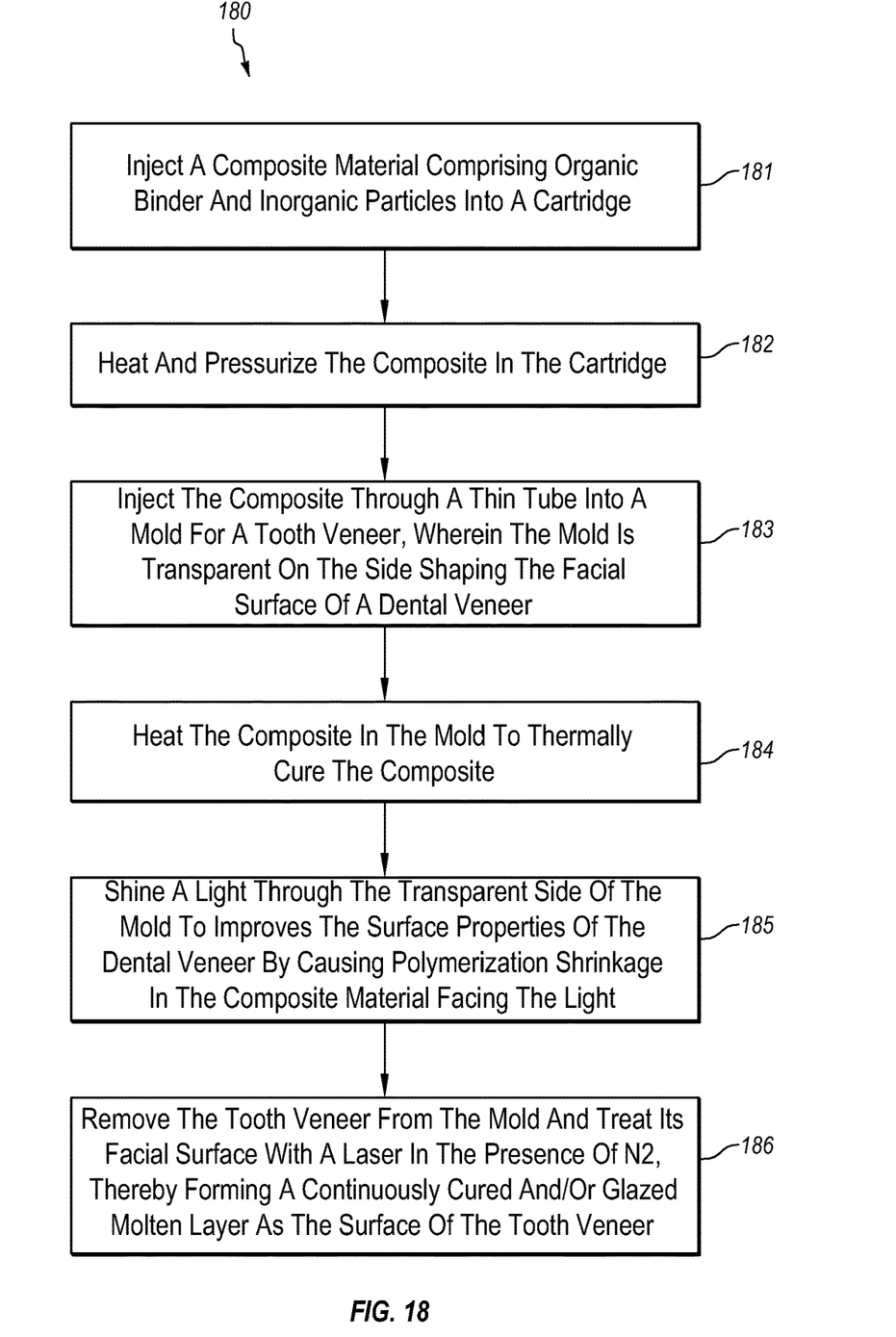
FIG. 18 is a flow diagram that schematically illustrates an exemplary method for treating a surface of a composite dental veneer to form a treated exterior surface.

FIG. 18 is a flow diagram that schematically illustrates an embodiment of an exemplary process 180 for molding and treating a dental veneer, which is expanded from the process 170 shown in FIG. 17. Specifically, in one or more embodiments of the invention, in step 181, the composite comprising the organic binder 2 and the solid particles 3 is first injected into a cartridge. In step 182, the composite is heated to an appropriate temperature (e.g., approximately 100° C.), which softens the composite for processing and molding. The composite may also be pressurized to a pressure between about 80-100 bars. Thereafter, in step 183, the composite in injected through a thin tube into a mold having the desired size and shape.

After the composite material is injected into the mold, in step 184 it is heated to an appropriate temperature (e.g., about 130° C.) and maintained at the temperature, the heating lasting for about 15 minutes to thermally cure the composite material. In step 185, during at least a portion of the duration of the heat curing process (e.g., the first 10 minutes or so of the about 15 minutes of thermal curing), light curing of the composite is performed on the facial surface of the veneer by shining light through a transparent side of the mold with a suitable LED light. In one or more embodiments of the invention, the suitable LED light is characterized, for example, by a wavelength from about 450 nanometers (nm) to about 480 nm. This curing step combines high pressure, heat, and light. The transparent side of the mold permits the curing light to pass through the mold to cure the facial side of the tooth veneer, which improves the surface properties of the veneer by causing polymerization shrinkage in the composite material facing the light. This shrinkage causes particles to become closer together on the facial surface of the veneer. Meanwhile, heating and high-pressure condense and consolidate particles together, resulting in high composite density throughout the dental veneer 1.

In one or more embodiments of the invention, the composite may comprise one or more photo initiators to facilitate the light curing process. Examples of suitable photo initiators include benzophenone, benzoin and derivatives thereof and a-diketones and derivatives thereof, such as 9,10-phenanthrenequinone, 1-phenyl-propan-1,2-dione, diacetyl and 4,4-dichlorobenzil. Camphorquinone, 2,2-methoxy-2-phenyl-acetophenone or α-diketones, each in combination with amines as reduction agents, such as e.g. 4-(dimethylamino)-benzoic acid esters, N,N-dimethylaminoethylmethacrylate, N,N-dimethyl-sym.-xylidine or triethanolamine, as well as monobenzoyl- or dibenzoyl germanium derivatives, are preferably used. To facilitate thermal curing, one or more heat initiators may be added to the composite in an embodiment of the invention. For instance, Benzopinacol and 2,2'-dialkylbenzopinacols are suitable as initiators for thermal curing.

In step 186, the blank of the dental veneer 1 is subsequently cooled and removed from the tooth mold, as illustrated. In one or more preferred embodiments of the invention, the veneer is placed in a compartment with $N_2$ gas, which prevents oxidation or burning of the organic binder. The facial area and/or the surface of the dental veneer 1 is then subjected to a laser treatment, wherein the laser is applied the facial surface of the veneer, entering the surface by about 80 μm and sintering the solid particles about 80 μm deep from other facial surface. During the laser processing of the facial areas the organic binder 2 is inhibited and/or removed from the surface of the dental veneer 1, and interstitial polymers are removed by vaporization. Coalescing of inorganic particles minimizes polymers on the facial surface of the veneer, forming a highly glossy surface develops based almost exclusively on the solid particles 3, which after the completion of the laser treatment forms a continuously cured and/or glazed molten layer as the surface of the dental veneer 1 (step 186). Care is taken in the process to prevent this cured and/or glazed molten layer from delaminating from underlying composite. In one or more embodiments of the invention, this layer is provable by a cross-section through the dental veneer 1 and preferably has a thickness ranging from about 10 to about 20 μm.

Figure 19:
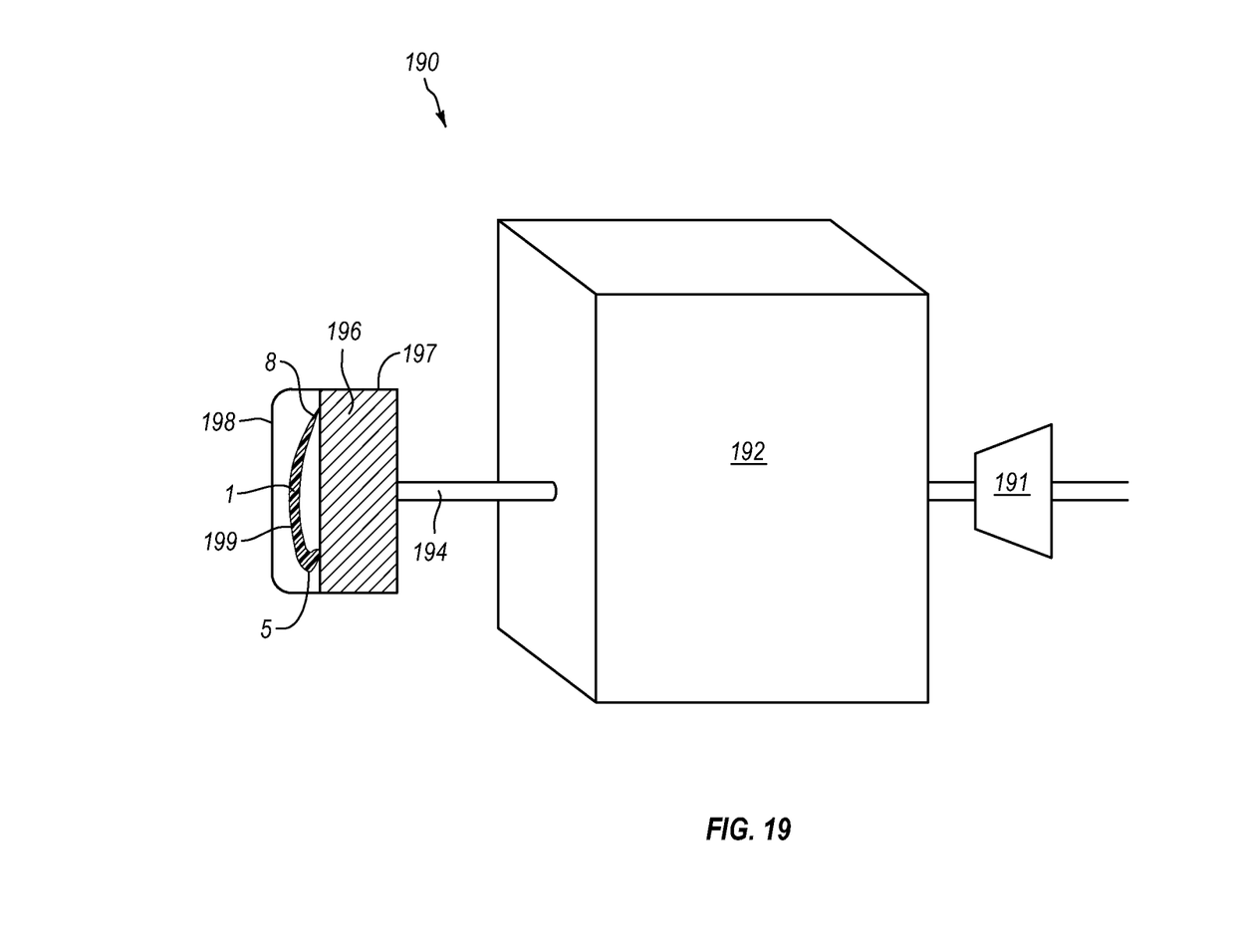
FIG. 19 is a schematic diagram illustrating an exemplary molding system for molding a dental veneer from a composite material.

In one or more embodiments of the invention, the mold for shaping the veneer is at least partially cup shaped. FIG. 19 schematically illustrates an example of a dental veneer mold system 190 according to the invention, wherein a mold 196 is connected through a thin tube 194 to a cartridge 192 containing a composite material pressurized by a pump 191. Although the cartridge 192 is illustrated as a box in FIG. 19, it can be embodied in various shapes and sizes known in the art. Similarly, the tooth veneer mold 196 may have various sizes, shapes, and configurations while effectively implementing the underlying principles of the current invention. Moreover, although the pressurizing pump 191 is illustrated as exterior to the cartridge 192, one skilled in the art understands that the pressurizing mechanism may be configured differently, either external or internal to the cartridge 192.

In a preferred embodiment of the invention, the mold 196 is transparent on the side 198 shaping the facial surface 199 of the dental veneer 1. The transparent side 198 of the mold 196 allows for light curing of the composite at the facial surface 199, and can be made of transparent materials such as inorganic or organic glasses. Because the composite material is also heated in the mold 196 for thermal curing, heat tolerant transparent material are suitable for making the mold 196. The opaque sides 197 of the mold 196 may be made of metals such as chromium-steel.

In one or more embodiments of the invention, it is advantageous to use a filler according to the invention based on a silanized glass in order to improve the mechanical properties of the cured dental material. The term "silanization" used herein means the functionalization of the glass surface with polymerizable silanes, such as by reaction with (meth)acrylate-functionalized silanes, e.g. (meth)acryloyloxyalkyl-trialkoxysilanes, usually 3-(methacryloyloxy)propyl-trimethoxy-silane, 3-(methacryloyloxy)-propyltriethoxysilane, 3-(methacryloyloxy)-propyltrichlorosilane, methacryloyloxy-methyltrimethoxysilane, methacryloyloxymethyltriethoxysilane, 3-(methacryloyloxy)-propylmethyldichlorosilane or 3-(meth-acryl-oyloxy)propylmethyldimethoxy silane. Among the examples of silanes above, 3-(Methacryloyloxy)-propyltrimethoxysilane is preferred. The silanization of the glasses takes place in conventional manner and is known to a person skilled in the art. Although it may be preferably to silanize all the filler particles, it may be desirable to not silanize nano-sized particles to prevent or minimize agglomeration.

In one or more embodiments of the invention, barium and/or strontium glass powder may be applied to coat the surface of the veneer during laser treatment. The laser vitrifies the glass powder and forms a glass layer on the facial surface of the veneer, which can match the hardness and refractive index of natural enamel. In these embodiments, the veneer has a heat cured composite base covered by a laser vitrified composite layer, which is covered by a barium and strontium glass layer.

Finally, cutting or post-processing of the cured composite may occur to yield the final product. The final processing may include, but are not limited to, cutting the veneer to achieve correct size and shape, grinding and/or smoothing edges and surface, and creating minute surface texture to achieve a realistic look instead of a perfectly uniform but fake look.

As an alternative to the above-described production method, it is also possible to cut the dental veneer 1 via laser from a block of composite material, which causes the cured and/or glazed molten layer to form automatically at the surface of the dental veneer 1.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing a dental veneer, comprising:
    shaping a composite material into a shape for attachment to a prepared tooth surface, the composite material comprising an organic binder and solid filler particles;
    at least partially hardening or curing the composite material; and
    laser treating a portion of the at least partially hardened or cured composite material to melt the solid filler particles at an exterior surface of the composite material, the solid filler particles of the exterior surface being continuously melted together to form a hardened glassy surface.

2. A method according to claim 1, wherein shaping the composite material and at least partially hardening or curing the composite material comprises:
    providing a moldable composite material;
    introducing the moldable composite material into a mold at high pressure, the mold at least partially corresponding to a desired shape of the dental veneer;
    subjecting the molded composite material within the mold to at least one of heat or light curing.

3. The method of claim 2, wherein the mold includes a glass surface corresponding to a facial surface of the dental veneer and a metal surface corresponding to a basal surface of the dental veneer.

4. The method of claim 3, wherein the method comprises both heat curing throughout the mold and light curing through the glass surface of the mold.

5. The method of claim 4, wherein light curing through the glass surface of the mold causes the composite material to undergo greater polymerization shrinkage adjacent to the glass surface as compared to adjacent to the metal surface, thereby causing solid filler particles at the facial surface of the dental veneer to be closer together than solid filler particles at the basal surface of the dental veneer.

6. The method of claim 1, further comprising placing the at least partially hardened or cured composite under nitrogen gas.

7. The method of claim 1, wherein laser treating causes at least a portion of the organic binder of the composite material to be removed so that the exterior surface has a higher percentage of solid filler particles than an adjacent composite region not laser treated.

8. The method of claim 1, wherein laser treating results in the exterior surface having an appearance resembling tooth enamel.

9. The method of claim 1, wherein laser treating results in the exterior surface being translucent.

10. The method of claim 1, wherein laser treating results in the exterior surface having a refractive index simulating natural tooth enamel.

11. The method of claim 1, further comprising applying glass powder to the dental veneer, wherein laser treating vitrifies the glass powder and forms a glass layer on the exterior surface.

12. The method of claim 11, wherein the glass powder comprises barium and/or strontium glass.

13. The method of claim 1, wherein the dental veneer has a hardness similar to that of natural teeth.

14. The method of claim 1, wherein laser treating results in the dental veneer having an L value of 59 to 69, an "a" value of −0.35 to −3.2, and a "b" value of −0.4 to −6.95.

15. The method of claim 1, wherein the organic binder comprise an acrylate or methacrylate.

16. The method of claim 1, wherein the solid filler particles comprise inorganic particles.

17. The method of claim 16, wherein the inorganic particles comprise one or more types of glass.

18. The method of claim 16, wherein the inorganic particles comprise differently sized particles having different grain sizes.

* * * * *